US006448435B1

(12) United States Patent
Jacobson et al.

(10) Patent No.: US 6,448,435 B1
(45) Date of Patent: Sep. 10, 2002

(54) SULFONATION, SULFATION, AND SULFAMATION

(75) Inventors: Stephen Ernest Jacobson, Princeton, NJ (US); David Richard Corbin, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/067,639

(22) Filed: Feb. 4, 2002

Related U.S. Application Data

(62) Division of application No. 09/848,842, filed on May 4, 2001, now Pat. No. 6,384,271.

(51) Int. Cl.$^7$ .......................... C07C 311/00; C07K 1/00
(52) U.S. Cl. ............................. 562/39; 562/37; 530/408
(58) Field of Search ...................... 562/37, 39; 530/408

(56) References Cited

U.S. PATENT DOCUMENTS

| T876,002 I4 | | 7/1970 | Smith |
|---|---|---|---|
| 3,544,619 A | * | 12/1970 | Yamaguchi |
| 4,117,004 A | * | 9/1978 | Fischer |
| 4,260,559 A | * | 4/1981 | Jacobs et al. |
| 4,290,974 A | * | 9/1981 | DuBois |
| 4,372,892 A | | 2/1983 | Fuchs et al. |
| 4,386,034 A | * | 5/1983 | Floyd et al. |
| 4,490,487 A | | 12/1984 | Halcour et al. |
| 4,705,845 A | * | 11/1987 | Cerami et al. |
| 4,775,587 A | | 10/1988 | Walles |
| 4,892,968 A | | 1/1990 | Campbell |
| 4,922,008 A | | 5/1990 | Seifert et al. |
| 5,233,081 A | | 8/1993 | Walles |
| 5,344,967 A | | 9/1994 | Schnur et al. |

FOREIGN PATENT DOCUMENTS

JP 04346932 12/1992

OTHER PUBLICATIONS

CA:74:99639 Abstract of DE2019250 Feb. 1971.
CA:77:60905 Abstract of Yuki Gosei Kagaku Kyokai Shi by Ogwa et al 30(3): 260–270 1972.
CA:84:60422 Abstract of JP50089284 Jul. 1975.
CA:90:121114 Abstract of J. Appl. Chem. Biotechnol. By Homsi et al 28 (6): 405–410 1978.
CA:90:121267 Abstract of Nippon Kagaku Kaishi by Shimura et al 11: 1532–1536 1978.
CA:96:103443 Abstract of Bull. Chem. Soc. Japan 54 (10): 3048–3058 1981.
CA:123:112973 Abstract of Macromolecules by Kumar et al 28 (8): 6323–6329 1995.
CA:133:150639 abs of Polish Journal of Chemistry by Mielniczak et al 74(6) pp. 785–791 2000.*

* cited by examiner

Primary Examiner—Jean F. Vollano

(57) ABSTRACT

A process that can be used for sulfonating, sulfating, or sulfamating an organic compound is disclosed. The process can comprise, consist essentially of, or consist of, contacting the organic compound with sulfur trioxide under a condition sufficient to effect the sulfonation, sulfation, or sulfamation of the organic compound. The organic compound can be an aromatic compound, alcohol, carbohydrate, amine, amide, protein, or combinations of two or more thereof. The sulfur trioxide can be present in a complex comprising an inorganic support such as zeolite, silicalite, silica, titanosilicate, borosilicate, clay, aluminophosphate, and combinations of two or more thereof.

18 Claims, No Drawings

SULFONATION, SULFATION, AND SULFAMATION

This is a divisional application of Ser. No. 09/848,842, filed May 4, 2001, now allowed as U.S. Pat. No. 6,384,271.

FIELD OF THE INVENTION

The invention relates to a process for sulfonating, sulfating, or sulfamating an organic compound.

BACKGROUND OF THE INVENTION

Sulfonation of organic compounds represents a major synthetic reaction. Sulfonations commonly use sulfuric acid and sulfur trioxide as the sulfonating agents. While sulfur trioxide presents major problems in terms of corrosivity, toxicity, and the consequences of leakage, it provides certain advantages. For example, sulfonation with sulfur trioxide can result in different and advantageous ratios of sulfonated isomers compared with the use of sulfuric acid and avoid safety problem with handling sulfuric acid.

The importance of the ratio of sulfonated isomers is conveniently described by the synthesis of p-cresol, extensively used in disinfectants and in the manufacture of resins. The sulfonation of toluene provides essentially a mixture of o- and p-toluene sulfonic acids, which are fused with sodium hydroxide to yield the corresponding o- and p-cresols (o- and p-methylphenols). Since the o-cresol is largely an unwanted byproducts, maximizing the ratio of para:ortho is highly advantageous in terms of ease of purification of the desired p-cresol, minimizing byproducts and waste streams, and minimizing energy use in the purification steps. The term regiospecificity is used to describe the ability of, in this application, a sulfonating agent, to affect the para:ortho ratio.

The sorption of sulfur trioxide by some basic organic compounds is well known. For instance, certain polyvinylpyridine resins form addition compounds with sulfur trioxide that can be used in sulfation reactions. See U.S. Pat. No. 3,057,855 disclosing use of a sulfur trioxide-poly(2-vinylpyridine) polymer for sulfation. See also W. Graf, in Chemistry and Industry, p 232, 1987 disclosing a pyridine-sulfur trioxide complex bound to a cross-linked polystyrene polymer and its use for the sulfation of alcohols and amines. However, the sulfur trioxide is sufficiently deactivated in the complexes that it does not sulfonate aromatics. Furthermore, U.S. Pat. No. 4,490,487 discloses $SO_3$ adducts with imides and the use of the adducts as sulfonating agents for aromatic compounds.

In all such complexes or adducts, $SO_3$ is deactivated. Some deactivate $SO_3$ enough that they become somewhat unreactive to sulfonate compounds that are relatively resistant to sulfonation. For instance, the sulfur trioxide-pyridine complexes described above have uses limited to the sulfation of alcohols, sugars, polysaccharides, etc.

It would be desirable to develop new sulfur trioxide complexes in which the sorbent is substantially insoluble to facilitate product isolation, which sulfonate aromatic compounds in a regiospecific manner, and which provide a more active solid sulfonating, sulfating, and sulfamating agent effective in a wider range of sulfonation, sulfation, and sulfamation processes.

An advantage of the invention is that it can be used industrially for the manufacture of detergents, dye intermediates, and sulfonated oils. For example, detergents can be made by using the $SO_3$ complexes disclosed below for either sulfating alcohols or sulfonating polyalkyl benzenes. Another advantage is that the use of the $SO_3$ complexes provides substantial safety and product isolation advantages over the prior art.

SUMMARY OF THE INVENTION

A process comprises contacting an organic compound with sulfur trioxide under a condition sufficient to effect the sulfonation, sulfation, or sulfamation of the organic compound in which the organic compound is selected from the group consisting of an aromatic compound, alcohol, carbohydrate, amine, amide, protein, and combinations of two or more thereof; and the sulfur trioxide is present in a complex comprising an inorganic support selected from the group consisting of zeolite, silicalite, silica, titanosilicate, borosilicate, clay, and combinations of two or more thereof.

DETAILED DESCRIPTION OF THE INVENTION

According to the invention, any organic compounds that can be sulfurized with $SO_3$ can be used. The term "sulfurized" refers to being added a sulfur atom or sulfur-containing functionality. Examples of suitable organic compounds include, but are not limited to, aromatic compounds, alcohols, carbohydrates, amines, amides, proteins, or combinations of two or more thereof.

The aromatic compound is preferably an activated aromatic compound. An activated aromatic compound has no substituents on the arylene ring or contains at least one electron-donating group on the arylene ring. Examples of electron-donating groups include alkyl, alkoxy, alkylthio, hydroxy, amino, amide such as —$NHCOCH_3$, phenyl, or combinations of two or more thereof. Specific examples of activated aromatic compounds include, but are not limited to, benzene, naphthalene, biphenyl, toluene, aniline, benzylamine, methylaniline, dimethylaniline, diphenylamine, triphenylamine, anisidines, acetanilide, benzanilide, toluidine, phenol, hydroxymethyl benzene, biphenyl, or combinations of two or more thereof. Many of these compounds such as, for example, aniline, benzylamine, methylaniline, dimethylaniline, toluidine, phenol, and hydroxymethyl benzene can also be sulfated or sulfamated. The presently preferred aromatic compound is toluene. See generally, Everett Gilbert, in "Sulfonation and Related Reactions", Interscience Publishers, John Wiley and Sons, 1965, p. 65.

The process of the invention is also useful for selectively sulfonating an aromatic compound. The term "selective or selectively" used herein, unless otherwise indicated, refers to the sulfonation of suitable aromatic compound to produce substantially higher para:ortho ratio. Such selective sulfonation is also referred to as improving "regiospecificity", which is disclosed in the BACKGROUND OF THE INVENTION section.

For example, with sulfonation of toluene using the invention process, the toluene sulfonic acid produced has an enhanced para:ortho ratio. Also, sulfonation of biphenyl, biphenyl-4-sulfonic acid production is enhanced. Further for example, selective sulfonation suppresses undesired multiple sulfonations in reactive aromatic compounds such as naphthalene.

Wishing not to be bound by theory, the mechanism for the regiospecificity is believed to be due to steric restrictions for a reaction within the inorganic support or sorbent pores. The pore dimensions are believed to orient the organic molecule as it contacts the sulfur trioxide. For instance, in the sulfonation of biphenyl, the biphenyl enters the pore constrained or oriented to present the 4-position to the reactant $SO_3$. The pore dimension creates a constraint against presentation of the 2- postion to the sorbed reactant; a constraint that is absent in conventional fluid phase reactions.

The preparation of p-cresol via the sulfonation of toluene and subsequent alkali metal hydroxide fusion discussed above is an example of sulfonation, which improves regiospecificity of the sorbed sulfur trioxide. The higher ratio of p-toluene sulfonic acid to o-toluene sulfonic acid results in a higher yield of the desired p-cresol and reduced isolation costs. A second example is the sulfonation of biphenyl, to give a sulfonation more regiospecific in the production of the preferred biphenyl-4-sulfonic acid, a source of various 4-substituted biphenyl compounds, including 4-phenylphenol.

Any alcohols that are substantially liquid or are soluble in an inert solvent under ambient conditions can be used. Examples of suitable alcohols include, but are not limited to, methanol, ethanol, propanol, isopropanol, butanol, isobutanol, pentanol, octanol, decanol, or combinations of two or more thereof.

Any carbohydrates that are substantially soluble in a solvent, which is inert to $SO_3$ such as super critical $CO_2$, can be used in the invention. Examples of suitable carbohydrates include, but are not limited to, glucose, fructose, sucrose, or combinations of two or more thereof.

Similarly, proteins suitable for use in the invention are substantially soluble in an inert solvent. Examples of suitable proteins also include peptides containing the repeat units of $(C(O)N(R))_n$ where R is hydrogen or a hydrocarbyl radical having 1 to about 10 carbon atoms per radical; and n can be a number from 2 to about 30.

Any amines and amides that can be sulfonated or sulfamated can be used in the invention. Examples of suitable amines include, but are not limited to, methylamine, ethylamine, propylamine, dimethylamine, ethylenediamine, tetraethylenediamine, ethanolamine, isobutylamine, those aromatic amines disclosed above, or combinations of two or more thereof.

Examples of suitable amides include, but are not limited to, acetamide, acrylamide, benzamide, formamide, propionamide, butyramide, valeramide, stearamide, succimmide, those aromatic amides disclosed above, or combinations of two or more thereof.

The organic compounds disclosed herein can be used in the presence of a solvent, if needed. A suitable solvent is inert to $SO_3$ and the organic compound. Suitable solvents can include, but are not limited to, methylene chloride, perfluorooctane, 1,2-dichloroethane, nitrobenzene, and liquid or supercritical carbon dioxide, or combinations of two or more thereof.

Sulfur trioxide can be incorporated into or supported on an inorganic support to produce a $SO_3$-inorganic support complex (hereinafter referred to as $SO_3$ complex) by any means known to one skilled in the art such as, for example, impregnation, sorption, or combinations thereof. The presently preferred method is a sorption process in which $SO_3$ is sorbed into the support.

The term "sorbed" used herein refers to a composition of an inorganic support and $SO_3$ exhibiting a partial vapor pressure of $SO_3$ less that that of sulfur trioxide itself, e.g., at 24° C. a partial vapor pressure of less than about 0.3 atmosphere (29 kPa).

The $SO_3$ complexes can be produced by sorbing sulfur trioxide into or onto an inorganic support. Any fluid containing 1 to about 100 weight % $SO_3$ can be used. The fluid can be gas, liquid, or combinations thereof such as nitrogen or $SO_3$, if pure is $SO_3$ used, and the preferred purity is from about 98 to 100%. Any source of $SO_3$ of adequate purity can be used, typically a container of pure liquid $SO_3$ is used. The $SO_3$, as vapor or liquid, is passed at a preferred temperature range of 35° C.–90° C. through a bed of an inorganic support to produce a $SO_3$ complex. The inorganic support can be heated up to 150° C. during the sorption or optionally heated and then cooled to increase sorption. The sorption process can be carried out with a suitable inorganic support in any suitable container or vessel inert to $SO_3$. Steel or stainless steel cylinders, which can be lined with an inert lining such as poly(tetrafluoroethylene), are preferred. Optionally an inert carrier gas may be used to move the sulfur trioxide into the sorbent. In a typical sorption step, for instance, dry nitrogen can be passed through liquid sulfur trioxide maintained at about 20° C. to about 50° C., preferably about 35° C., to provide a stream containing about 50% by volume of $SO_3$.

The term "inert fluid or gas" refers to a fluid or gas that is unreactive with $SO_3$, support, or container, such as nitrogen. When an inert gas is used, the purity of the $SO_3$ is described exclusive of the carrier gas. Optionally $SO_3$ can be sorbed under a positive pressure to accelerate sorption.

Sulfur trioxide suitable for use in the invention can be incorporated in or supported on an inorganic support. Examples of such inorganic supports include, but are not limited to, zeolites, silicalites, silicas, titanosilicates, borosilicates, clays, aluminophosphates, or combinations of two or more thereof.

Molecular sieves, both natural and synthetic, are well known in the art. See, e.g., R. Szostak, Molecular Sieves—Principles of Synthesis and Identification, Van Nostrand Reinhold (1989). The inorganic molecular sieves used for incorporating or supporting sulfur trioxide include various silicates (e.g., titanosilicates, borosilicates, silicalites, low alumina-containing zeolites such as mordenite and ZSM-5, and high alumina-containing zeolites such as 5A, NaY and 13X). The preferred molecular sieves are either acidic or are non-acidic silicates.

Zeolites are available from various sources. A comprehensive listing of zeolites vendors is contained in "CEH Marketing Research Report: Zeolites" by M. Smart and T. Esker with A. Leder and K. Sakota, 1999, Chemical Economics Handbook-SRI International.

Examples of suitable zeolites include, but are not limited to, mordenite, Y, X, 5A, US-Y, DA-Y, ZSM-5, ZSM-11, beta, L, ferrierite, and clinoptilolite. Examples of suitable titanosilicates are TS-1, TS-2, and Ti-beta. Examples of suitable clays are montmorillonite, kaolin, and talc. Examples of suitable borosilicates are boralite-A, boralite-B, boralite-C, and boralite-D. Examples of suitable aluminophosphates are $AlPO_4$-5, SAPO-5, $AlPO_4$- 11, SAPO-34, and combinations of two or more thereof. Silicas include precipitated silica, dried silica, diatomaceous earth, silica gels, and fumed silicas. See also Kirk-Othmer Encyclopedia of Chemical Technology, $3^{rd}$ edition, volume 115 (John Wiley & Sons, New York, 1991) and W. M. Meier and D. H. Olson, "Atlas of Zeolite Structure Types", $3^{rd}$ edition (Butterworth-Heineman, Boston, Mass. 1992).

The pore dimensions that control access to the interior of the zeolite are determined not only by the tetrahedra forming the pore opening, but also by the presence or absence of ions in or near the pore. In the case of zeolite A, for example, access can be restricted by monovalent ions, such as $Na^+$ or K+, which are situated in or near 8-ring openings as well as 6-ring openings. Access is enhanced by divalent ions, such as $Ca^{2+}$, which are situated only in or near 6-ring openings. Thus, the potassium and sodium salts of zeolite A exhibit effective pore openings of about 0.3 nm and 0.4 nm respectively, whereas the calcium salt of zeolite A has an effective pore opening of 0.5 nm. For this application it is important that the pore opening be of sufficient size (at least 0.5 nm) to allow the ingress and egress of sulfur trioxide. The presence or absence of ions in or near the pores, channels, and/or cages can also significantly modify the accessible pore volume of the zeolite for sorbing materials. To maximize capacity, generally protons or small cations are preferred.

Preferred inorganic supports include high surface area silicas and high silica-containing molecular sieve materials (Si/Al greater than about 5.1) prepared either by synthesis or modification. These materials include silicalite, mordenite, beta, US-Y, DA-Y, ZSM-5, ZSM-11, borosilicates, titano-silicates and the like. The most preferred materials have a Si/Al ratio of at least about 25. Those with Si/Al ratios in the range from about 1 to about 4.4 can also be used. The amount of sulfur trioxide incorporated or supported is at least about 1%, preferably at least about 3%, and most preferably at least about 5% by weight, based on the weight of the supports. The maximum amount is dependent upon the physical structure of the support used, typically in the range from about 40% to about 60% based on the weight of the support.

Because these inorganic supports are well known to one skilled in the art, the description of which is omitted herein for the interest of brevity.

Preferably, the support is in a pelletized, beaded, or extruded and chopped form to facilitate gas or liquid flow through. It can be pelletized, beaded, or extruded using a suitable binder, which is stable to exposure to sulfur trioxide and the sorption/desorption conditions, using any means well known to one skilled in the art. Gamma-alumina, silica, and clays are examples of suitable binders.

The processes of sulfonation and sulfation can be carried out by any means known to one skilled in the art such as that disclosed in detail in "Sulfonation and Sulfation" in The Encyclopedia of Chemical Technology, 4th edition, Wiley Interscience Publication, John Wiley & Sons, New York N.Y., 1997. Both are methods for the introduction of the $SO_3$ group into organic compounds. In sulfonation, the $SO_3$ group is introduced to produce a sulfonate, where the $SO_3$ group is bound directly to a carbon atom, yielding a C—$SO_3$—X structure. X can be hydrogen, a metal (sulfonate salt), or halogen (sulfonyl halide). Sulfonation of toluene with sulfur trioxide, as an example, yields toluene sulfonic acid isomers. In sulfation, the $SO_3$ group is introduced to produce a sulfate, where the $SO_3$ group is bound though an oxygen atom to a carbon atom, yielding a C—O—$SO_3$—X group. For example, sulfation of an alcohol with sulfur trioxide yields the alcohol sulfate. Sulfamation is the sulfonation of the $R_2NH$ group in amines, amides, and proteins to form a $R_2NSO_3H$ group.

The organic compound to be sulfonated, sulfated, or sulfamated can be contacted with a $SO_3$ complex under a condition sufficient to sulfonate, sulfate, or sulfamate the organic compound. The organic compound can be present as a fluid, vapor, liquid, solution, or combinations thereof both, with or without a solvent disclosed above or in a carrier gas such as nitrogen. For example, sulfonation using the $SO_3$ complexes can be carried out by heating the organic compound alone or in an inert solvent with the $SO_3$ complex to effect reaction. Any of the solvents disclosed above (methylene chloride, perfluorooctane, 1,2-dichloroethane, nitrobenzene, and liquid or supercritical carbon dioxide) can be used. The condition can include a temperature in the range of from about 0 to about 100° C., preferably 20 to 60° C., under a pressure that can accommodate the temperature range for a period of time in the range of from about 1 to about 100 hours, preferably 10 to 50 hours. The molar ratio of sorbed $SO_3$ to the organic compound can be in the range from about 0.01:1 to about 100:1, preferably 1:10 to 10:1. An excess of organic compound can be used to function as a solvent. An excess of the sorbed $SO_3$ can be used where it is desirable to force complete reaction of the organic compound. A ratio of about 1:1 is generally preferred in a continuous pipeline counter-current reactor.

When the sulfonation, sulfation, or sulfamation is complete, the product can be isolated conventionally. For instance, the residual inorganic sorbent or support is filtered off, washed with water, and the filtrate extracted with sufficient amount of water to remove the sulfonated, sulfated, or sulfamated product. The sulfonated, sulfated, or sulfamated product can be isolated from the combined extracts conventionally by any means known to one skilled in the art and water can be removed to isolate the product.

EXAMPLES

Example 1

This Example Shows the Sulfonation of Toluene Using a Silica Gel/$SO_3$ Complex

A sample (20 g) of silica gel (Grade 952, a silica gel from Davison Division of W. R. Grace, Baltimore Md.) was placed in a quartz tube in a vertically mounted tube furnace, heated by raising the temperature 60° C. per hour to 600° C. and holding at 600° C. (the drying temperature) for 5 hours under flowing nitrogen. The sample was cooled under flowing nitrogen and then transferred to a dry box. This procedure was repeated as necessary and dried material from each run was combined and mixed thoroughly.

A polytetrafluoroethylene (PTFE) vessel was loaded with 32.6 g (initial weight) of the dried silica gel and heated to 60° C. Distilled $SO_3$ vapor (at 44° C.) was purged over the solid for 2 hours. The solid was then heated to 78° C. under a dry nitrogen purge for 11.5 hours to remove surface bound $SO_3$. The final weight of the silica gel/$SO_3$ complex was 36.4 g (11.5% weight gain, 10.4% $SO_3$ loading). The silica gel/$SO_3$ complex was the n transferred under anhydrous conditions to the thermogravimetric analysis (TGA) where on average it lost 9.4% of its weight between room temperature and 350° C.

The silica gel/$SO_3$ (5.0 g, containing 7.5 mmol sulfur trioxide, sorbant quantity/mmol $SO_3$) was added to toluene (50.0 g, substrate/weight) under nitrogen in a 1000-ml round bottomed flask equipped with overhead stirrer and condenser. The solution was then heated to 50° C. for 20 hours (reaction temperature/time). The solution was cooled to room temperature and the silica gel support was filtered from the solution. The gel was washed with 10 ml hot water (60° C.) and the toluene was extracted with the same water solution. The water was analyzed by high pressure liquid chromatography (HPLC) and shown to contain 29% yield p-toluenesulfonic acid (TSA), 4% O-TSA, and 0.7% m-TSA (ratio p/o=7.3) for a total 33.7% yield (product % yield) based on the $SO_3$ in the complex.

Examples 2–11

Examples 2–11 were Carried Out Similarly as Example 1

Experimental details of all Examples are shown in Table 1. Product details of these Examples are shown in Table 2.

In Table 1, the sorbents and sources are as follows. Examples 1, 9, 10, and 11: silica gel (Grade 952, a silica gel from Davison Division of W. R. Grace, Baltimore, Md.); Examples 2 and 8: silicalite (S-115), from Union Carbide, New York, N.Y.; now UOP, Des Plaines, Ill.; Example 3: H-Beta ($SiO_2/Al_2O_3$=25) (CP 811BL-25, H-beta ($SiO_2/Al_2O_3$=25), PQ Corp., Valley Forge, Pa.; Example 4: high silica Y-zeolite (CBV-901, a H-SDUSY zeolite ($SiO_2/Al_2O_3$=150) from Zeolyst International, Valley Forge, Pa.; Example 5: H-ZSM-5 zeolite ($SiO_2/Al_2O_3$=150), from Conteka, Leiden, Netherlands, now Zeolyst International, Valley Forge, Pa.); Example 6: H-ZSM-olite ($SiO_2/Al_2O_3$=300) from PQ Corp., Valley Forge, Pa.; and Example 7: Zeolite 5A (Molecular Sieve Type 5A), from Linde Division, Union Carbide, New York N.Y., now UOP, Des Plaines, Ill.

The toluene and oil layer was extracted with three 10-cc portions of distilled water. The analysis by HPLC showed 28% yield of p-TSA and 5.5% o-TSA (ratio p/o=5.1) for a total yield of 33.5%.

Comparative Example C

This Example Illustrates Preparation of Silica Gel/$H_2SO4$ Complex and Demonstrates that Sulfonation is not Effective with a Sulfuric Acid Complex As described in the literature [F. Chavez et al, Synthetic Communications, 24(16), 2325–2339(1994)], silica gel (10 g), sulfuric acid (1.20 g), and acetone (50 g) were stirred in a 100 ml round bottom flask equipped with condenser, magnetic stirrer, and thermocouple at room temperature for

TABLE 1

Experimental Detail for Examples 1–11

| Ex. | | | $SO_3$ Sorption | | | Catalyst Utilization (see Table 2 for product detail) | | | |
|---|---|---|---|---|---|---|---|---|---|
| # | Sorbent[1] | T[2] | W[3] | G/L[4] | WL[5] | S/W[6] | Q[7] | R[8] | Y[9] |
| 1 | Silica | 600 | 32.6/36.4 | 11.7/10.4 | 9.4 | T/50 | 5.0/7.5 | 50/20 | TSA/33.7 |
| 2 | Silicalite | 500 | 5.0/5.9 | 18.0/15.3 | 15.2 | T/75 | 3.2/6.0 | 50/20 | TSA/35.9 |
| 3 | H-beta | 500 | 5.5/6.62 | 20.4/16.9 | 13.7 | T/75 | 3.4/6.0 | 50/20 | TSA/38.9 |
| 4 | Y-zeolite | 500 | 3.0/4.3 | 43.3/30.2 | 29.1 | T/50 | 2.0/7.3 | 50/20 | TSA/25.5 |
| 5 | H-ZSM-5 | 500 | 30.7/33.9 | 10.4/9.4 | 14.1 | T/50 | 5.0/8.8 | 50/20 | TSA/30.7 |
| 6 | H-ZSM-5 | 500 | 30.1/33.1 | 10.0/9.1 | 9.0 | T/50 | 5.0/5.6 | 50/20 | TSA/30.9 |
| 7 | Zeolite 5A | 500 | 10.5/11.4 | 8.6/7.9 | 8.8 | T/50 | 3.99/7.5 | 50/20 | TSA/53.9 |
| 8[10] | | | As Ex. 2 | | | T/2 | 2.52/6.8 | 40/20 | TSA/41.1 |
| 9[11] | | | As Ex. 1 | | | B/3.9 | 5.3/6.3 | RT/22 | BPS/29.7 |
| 10 | As Ex. 1 | 600 | 20.0/23.9 | 19.5/16.3 | 17.4 | M/20 | 2.5/6.25 | RT/1 | MSA/68.5 |
| 11 | | | As Ex. 1 | | | Bu/20 | 2.5/6.25 | RT/1 | BSA/82.4 |

[1]See listing at Example 1 for sources & specifications.
[2]T, drying temp. for 5 h (°C.)
[3]W, initial weight/final weight (g)
[4]G/L, $SO_3$ gain/load (%)
[5]WL, weight Loss to 350° C. (%)
[6]S/W, substrate or reactant in grams; T, toluene; B, biphenyl; M; methanol; Bu, butanol.
[7]Q, $SO_3$/sorbant Quantity (g)/mmol $SO_3$
[8]R, reaction temperature/time (°C./h); RT: room temperature.
[9]Product % yield; TSA: toluene sulfonic acid isomers; BPS: biphenyl 4-sulfonic acid; MSA: methyl sulfate; BSA: n-butyl sulfate.
[10]Example 8 used toluene (2 g) dissolved in dry methylene chloride (25 g) and was refluxed at 40° C. The product was extracted with acetonitrile instead of water.
[11]Example 9 used biphenyl (3.9 g) dissolved in dry methylene chloride (50 g).

Comparative Example A

This Example Shows Sulfonation of Toluene Using 98% Sulfuric Acid

Sulfuric acid (1.0 g, 10.2 mmol) was added to toluene (50.0 g) under the same conditions as Example 1. The analysis by HPLC showed 26% yield p-toluenesulfonic acid, 11% o-toluenesulfonic acid, and 1.3% m-toluenesulfonic acid (ratio p/o=2.4) for a total yield of 38.3%.

Comparative Example B

This Example Shows Sulfonation of Toluene Using Sulfur Trioxide

Sulfur trioxide (0.6 g, 7.5 mmol, stabilized, 99% from Aldrich, Milwaukee, Wis.) was weighed into a 100-ml round-bottom flask in the dry box. Toluene (50 g) was added to the sulfur trioxide via syringe under an inert atmosphere. The solution was stirred at 50° C. for 22 hours under a nitrogen atmosphere before it was cooled to room temperature. A dark colored oil formed at the bottom of the solution.

2 hours. The acetone was removed under vacuum and the silica gel was removed under vacuum at 80° C. The TGA analysis showed 1.44 mmol $H_2SO_4$/g silica.

Silica gel/$H_2SO_4$ complex prepared as described above (5.0 g, 7.2 mmol) was added under nitrogen to dried toluene (50 g) in a 100-ml round-bottom flask equipped with a magnetic stirrer, condenser, gas inlet, thermocouple, and heating mantle. The solution was heated to 50° C. for 18 hr, cooled to room temperature, and filtered. The toluene was extracted with three 10-ml portions of water. The insoluble support was placed into the thimble of a Soxhlet Extractor with 100-ml water and extracted for 48 hours. The combined water extracts were analyzed by HPLC and shown to contain 0.9% p-TSA, 0.01% o-TSA, and trace m-TSA for a TSA total yield of 0.9%.

Comparative Examples D and E

These Examples Show that Silicalite/$SO_3$ Reacts with Other Solvents such as Acetonitrile and Tetrahydrofuran Comparative Example D was prepared in the same way as Example 8 using the silicalite/$SO_3$ complex prepared as in Example 2, but used dried acetonitrile (50 g) rather than methylene chloride. The HPLC analysis showed 4.2% p-TSA, 0.52% o-TSA, and 0.1% m-TSA for a total TSA yield of 4.8%. Only small amounts of sulfur (1.6%) were left in the zeolite by x-ray fluorescence elemental analysis, indicating complete reaction of the sulfur trioxide.

Comparative Example E was prepared in the same way as Example 8 using the silicalite/$SO_3$ complex prepared as in Example 2, but used dried tetrahydrofuran (50 g) rather than methylene chloride. The HPLC analysis showed 4.8% p-TSA, 1.2% o-TSA, and 0.09% m-TSA for a total TSA yield of 6.1%. Only small amounts of sulfur (0.9%) were left in the zeolite by x-ray fluorescence elemental analysis indicating complete reaction of the sulfur trioxide. The gas chromatography/mass spectrometric analysis also showed that tetrahydrofuran was sulfonated.

The results of the examples and comparative examples are shown in Table 2.

TABLE 2

Comparison of Isomer Yields and Ratios

| Example (solvent) | Toluene Sulfonic Acid Isomers | | | Yield (%) | p:o ratio | p:o ratio improvement factor vs. Comp. Example A |
|---|---|---|---|---|---|---|
| | Ortho (o) | Meta (m) | Para (p) | | | |
| Examples | | | | | | |
| 1 | 4.0 | 0.7 | 29 | 33.7 | 7.3 | 3.0 |
| 2 | 1.8 | 0.1 | 34 | 35.9 | 18.9 | 7.9 |
| 3 | 4.0 | 0.7 | 34.2 | 38.9 | 8.6 | 3.6 |
| 4 | 6.6 | 0.5 | 18.4 | 25.5 | 2.8 | 1.2 |
| 5 | 3.9 | 0.4 | 26.4 | 30.7 | 6.8 | 2.8 (0.7% sulfone) |
| 6 | 1.9 | 0.2 | 28.8 | 30.9 | 15.2 | 6.3 |
| 7 | 7.7 | 0.7 | 45.5 | 53.9 | 5.9 | 2.2 |
| 8 ($CH_2Cl_2$) | 9.6 | 1.3 | 30.2 | 41.1 | 3.1 | 1.3 (0.04% sulfone) |
| Comparative Examples | | | | | | |
| A | 11.0 | 1.3 | 26 | 38.3 | 2.4 | — |
| B | 5.5 | * | 28.0 | 33.5 | 5.1 | |
| C | 0.01 | * | 0.9 | 0.9 | | Poor yield |
| D ($CH_3CN$) | 0.52 | 0.1 | 4.2 | 4.8 | | Poor yield |
| E (THF**) | 1.2 | 0.09 | 4.8 | 6.1 | | Poor yield |

*Trace of isomer detected but in less than a quantifiable concentration.
**THF, Tetrahydrofuran.

Table 2 shows substantially enhanced para/ortho ratios for the sulfonation of toluene to toluene sulfonic acid using the invention process.

What is claimed is:

1. A process comprising contacting an organic compound with sulfur trioxide under a condition sufficient to effect the sulfamation of said organic compound wherein said organic compound is selected from the group consisting of amine, amide, protein, and combinations of two or more thereof; and said sulfur trioxide is present in a complex comprising an inorganic support selected from the group consisting of zeolite, silicalite, silica, titanosilicate, borosilicate, clay, aluminophosphate, and combinations of two or more thereof.

2. A process according to claim 1 wherein said organic compound is selected from the group consisting of aniline, benzylamine, methylaniline, dimethylaniline, diphenylamine, triphenylamine, anisidines, acetanilide, benzanilide, toluidine, aminobenzene, methylamine, ethylamine, propylamine, dimethylamine, ethylenediamine, tetraethylenediamine, ethanolamine, isobutylamine, acetamide, acrylamide, benzamide, formamide, propionamide, butyramide, valeramide, stearamide, succinimide, and combinations of two or more thereof.

3. A process according to claim 2 wherein said sulfur trioxide is present in a complex comprising an inorganic support selected from the group consisting of silica gel, silicalite, beta-zeolite, H-SDUSY zeolite, H-ZSM-5, 5A molecular sieve, and combinations of two or more thereof.

4. A process according to claim 3 wherein the molar ratio of said organic compound to sulfur trioxide is in the range of from 0.1:1 to 10:1.

5. A process according to claim 1 wherein the weight percent of said sulfur trioxide is in the range of from about 5% to about 45% based on the total weight of said sulfur trioxide and said inorganic support equaling 100%.

6. A process according to claim 4 wherein the weight percent of said sulfur trioxide is in the range of from about 5% to about 45% based on the total weight of said sulfur trioxide and said inorganic support equaling 100%.

7. A process according to claim 1 wherein said process is carried out in the presence of a solvent selected from the group consisting of methylene chloride, carbon dioxide, perfluorooctane, 1,2-dichloroethane, nitrobenzene, and combinations of two or more thereof.

8. A process according to claim 2 wherein said process is carried out in the presence of a solvent selected from the group consisting of methylene chloride, carbon dioxide, perfluorooctane, 1,2-dichloroethane, nitrobenzene, and combinations of two or more thereof.

9. A process according to claim 4 wherein said process is carried out in the presence of a solvent selected from the group consisting of methylene chloride, carbon dioxide, perfluorooctane, 1,2-dichloroethane, nitrobenzene, and combination of two or more thereof.

10. A process according to claim 6 wherein said process is carried out in the presence of a solvent selected from the group consisting of methylene chloride, carbon dioxide, perfluorooctane, 1,2-dichloroethane, nitrobenzene, and combinations of two or more thereof.

11. A process according to claim 1 wherein said process is carried out in the presence of an inert fluid selected from the group consisting of nitrogen, helium, carbon dioxide, and combinations of two or more thereof.

12. A process according to claim 10 wherein said process is carried out in the presence of an inert fluid selected from the group consisting of nitrogen, helium, carbon dioxide, and combinations of two or more thereof.

13. A process comprising contacting an organic compound with sulfur trioxide under a condition sufficient to effect the sulfamation of said organic compound wherein said organic compound is selected from the group consisting of aniline, benzylamine, methylaniline, dimethylaniline, diphenylamine, triphenylamine, anisidines, acetanilide, benzanilide, toluidine, aminobenzene, methylamine, ethylamine, propylamine, dimethylamine, ethylenediamine, tetraethylenediamine, ethanolamine, isobutylamine, acetamide, acrylamide, benzamide, formamide, propionamide, butyramide, valeramide, stearamide, succinimide, and combinations of two or more thereof; and said sulfur trioxide is present in a complex comprising an inorganic support selected from the group consisting of zeolite, silicalite, silica, titanosilicate, borosilicate, clay, aluminophosphate, and combinations of two or more thereof.

14. A process according to claim 13 wherein said inorganic support is selected from the group consisting of silica gel, silicalite, beta-zeolite, H-SDUSY zeolite, H-ZSM-5, 5A molecular sieve, and combinations of two or more thereof.

15. A process according to claim 13 wherein said process is carried out in the presence of an inert fluid selected from the group consisting of nitrogen, helium, carbon dioxide, and combinations of two or more thereof.

16. A process according to claim 14 wherein said process is carried out in the presence of an inert fluid selected from the group consisting of nitrogen, helium, carbon dioxide, and combinations of two or more thereof.

17. A process according to claim 13 wherein said process is carried out in the presence of an inert fluid selected from the group consisting of nitrogen, helium, carbon dioxide, and combinations of two or more thereof.

18. A process according to claim 16 wherein said process is carried out in the presence of an inert fluid selected from the group consisting of nitrogen, helium, carbon dioxide, and combinations of two or more thereof.

* * * * *